United States Patent [19]

Hedengren et al.

[11] Patent Number: 5,389,876
[45] Date of Patent: Feb. 14, 1995

[54] FLEXIBLE EDDY CURRENT SURFACE MEASUREMENT ARRAY FOR DETECTING NEAR SURFACE FLAWS IN A CONDUCTIVE PART

[75] Inventors: Kristina H. V. Hedengren; Richard O. McCary, both of Schenectady, N.Y.; Robert P. Alley, Myrtle Beach, S.C.; Richard J. Charles, Schenectady, N.Y.; William P. Kornrumpf, Albany, N.Y.; John D. Young, Rexford, N.Y.

[73] Assignee: General Electric Company, Schenectady, N.Y.

[21] Appl. No.: 696,455

[22] Filed: May 6, 1991

[51] Int. Cl.[6] .................... G01N 27/82; G01R 33/12
[52] U.S. Cl. .................................. 324/242; 324/262
[58] Field of Search ............... 324/238, 239, 240, 241, 324/242, 243, 262, 226

[56] References Cited

U.S. PATENT DOCUMENTS

| | | |
|---|---|---|
| 3,271,662 | 8/1962 | Quittner. |
| 3,437,918 | 2/1967 | Arnelo. |
| 4,547,962 | 10/1985 | deWalle et al. |
| 4,593,245 | 6/1986 | Viertl et al. ............... 324/238 |
| 4,706,021 | 11/1987 | Chamuel .................. 324/242 |
| 4,965,519 | 10/1990 | Tornblom ................. 324/225 |
| 5,047,719 | 9/1991 | Johnson et al ............ 324/242 |

FOREIGN PATENT DOCUMENTS

| | | |
|---|---|---|
| 0228177 | 11/1986 | European Pat. Off. |
| 0381848 | 8/1990 | European Pat. Off. |
| 0113947 | 9/1980 | Japan ....................... 324/241 |
| 0673896 | 4/1990 | Switzerland .............. 324/242 |
| 700830 | 11/1979 | U.S.S.R. ................... 324/238 |

OTHER PUBLICATIONS

"Miniature Multilayer Spiral Inductors for GaAs MMICs", Geen et al., GaAs IC Symposium, Technical Digest 1989, San Diego, Calif. Oct. 22-25, 1989, pp. 303-306.

"Inspection of Electrically Conducting Objects with Eddy-Current Facilities", Shaternikov et al., The Soviet Journal of Nondestructive Testing, Jun. 1987, No. 6, New York, N.Y., USA, pp. 412-413.

"Eddy Current Imaging for Defect Characterization," David C. Copley, GE/Aircraft Engine Business Group, Evendale, Ohio, Review of Progress in Quantitative Nondestructive Evaluation, vol. 2B, Plenum Press, New York, 1983, pp. 1527-1540.

"Eddy Current Imaging," R. O. McCary, D. W. Oliver, K. H. Silverstein, and J. D. Young, IEEE Transactions on Magnetics, vol. MAG-20, No. 5, Sep. 1984, pp. 1986-1988.

"Eddy Current Imaging of Surface-Breaking Structures," R. E. Joynson, R. O. McCary, D. W. Oliver, K. H. Silverstein-Hedengren, L. L. Thumhart, GE/CR&D, Schenectady, N.Y., IEEE Transactions on Magnetics, vol. MAG-22, No, 5, Sep. 1986, pp. 1260-1262.

(List continued on next page.)

Primary Examiner—Walter E. Snow
Attorney, Agent, or Firm—Paul R. Webb, II

[57] ABSTRACT

An eddy current probe array is disclosed comprising a plurality of spatially correlated eddy current probe elements sufficiently disposed within a flexible interconnecting structure to collect a discrete plurality of spatially correlated eddy current measurements for nondestructive near surface flaw detection. A plurality of precisely fabricated, substantially identical elements being sufficiently distributed can accommodate inspecting an area of conductor covered by the active width of the array in a single uni-directional scan. The array structure can flexibly conform to accommodate inspection of large, irregular, curved conductive surfaces which cannot be inspected by conventional means.

29 Claims, 13 Drawing Sheets

OTHER PUBLICATIONS

"Use of Imaging Techniques for Eddy Current NDE," K. H. Hedengren, R. O. McCary and J. D. Young, GE/CR&D, Schenectady, N.Y., Review of Progress in Quantitative Nondestructive Evaluation, vol. 7A, Edited by Donald Thompson and Dale E. Chimenti (Plenum Publishing Corp., 1988) pp. 357–365.

"Flexible Substrate Eddy Current Coil Arrays," Y. D. Krampfer and D. D. Johnson, Review of Progress in Quantitative Nondestructive Evaluation, vol. 7A, pp. 471–478, 1988.

"Eddy Current Probe Evaluation: Experimental Measurements & System Interaction," K. H. Hedengren, R. O. McCary and J. D. Young, GE/CR&D, Schenectady, N.Y., Review of Progress in Quanitiative Nondestructive Evaluation, vol. 8A, Edited by Donald O. Thompson and Dale E. Chimenti (Plenum Publishing Corp., 1988).

"Eddy Current Probe Analysis," T. G. Kincaid, Signametrics Report No. 7, Mar. 12, 1987 (also appearing as an appendix in a GE Final Report).

"Eddy Current Printed Circuit Probe Array: Phase IIA," T. G. Kincaid, Signametrics Report No. 10, Dec. 29, 1988 (also appearing in a GE Final Report No. 2880582Y20XG, Eddy Current Technology Department, Jan. 1989 as an appendix).

"Automating an Eddy Current Test System for In-Service Inspection of Turbine/Generator Rotor Bores," R. O. McCary, J. R. M. Viertl, GE/CR&D and GE/Power Generation, Schenectady, New York, IEEE Transactions on Magnetics, vol. 24, No. 6, Nov. 1988, pp. 2594–2596.

"Eddy Current Image Processing for Crack Size Characterization," R. O. McCary, GE Co., Corporate Research and Development, Review of Progress in Quantitative Nondestructive Evaluation, vol. 8A, Edited by D. O. Thompson and D. E. Chimenti, Plenum Press, New York, 1990, pp. 773–780.

"Eddy Current Printed Circuit Probe Array:Phase I," T. G. Kincaid, Signametrics Report No. 9, Sep. 12, 1987 (also appeared as an appendix to a GE final report).

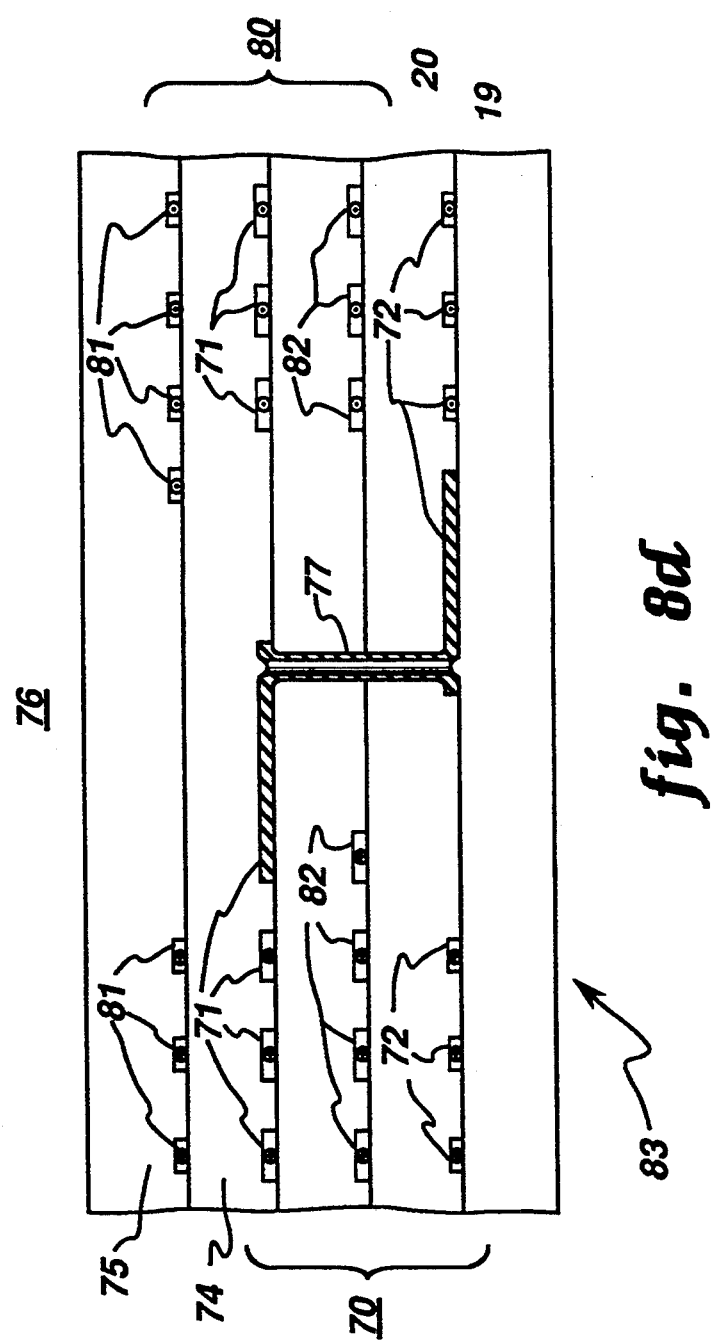

FLEXIBLE EDDY CURRENT SURFACE MEASUREMENT ARRAY FOR DETECTING NEAR SURFACE FLAWS IN A CONDUCTIVE PART

RELATED APPLICATIONS

The present application is related to patent application Ser. No. 07/696,456, now U.S. Pat. No. 5,182,513 entitled "Method and Apparatus for Nondestructive Surface Flaw Detection" by John D. Young et al, which discloses and claims a method and apparatus for acquiring a plurality of synchronized, spatially correlated, discrete eddy current measurement signals for image processing. Application Ser. No. 07/696,457, now U.S. Pat. No. 5,237,271 entitled "Multi-frequency Eddy Current Sensing" by Kristina H. Hedengren, discloses and claims a method for improving resolution and characterization in detection of near surface flaw using nondestructive eddy current inspection. Both referenced applications are assigned to the same assignee as the present application and are filed concurrently herewith being incorporated herein by reference in their entireties.

Co-pending application Ser. No. 07/504,769, now abandoned entitled "A Flexible Interconnected System" by Charles W. Eichelberger, et al describes a multi-layer, multi-component integrated fabrication technology suitable for making flexible, spatially correlated, eddy current probe arrays for inspecting difficult surface geometries. This co-pending application is assigned to the same assignee as the present application and is incorporated herein by reference in its entirety.

FIELD OF INVENTION

This invention relates generally to eddy current probe arrays and more particularly to precisely alike probe elements encapsulated in a flexible, multi-layer, integrated eddy current probe array.

BACKGROUND

Nondestructive eddy current technology is an established technology and various inspection systems exist. Typical systems utilize coupled, multi-turn induction coils often surrounding ferrite cores to intensify induced magnetic field flux. One of the induction coils, the drive coil, is disposed very near the surface of a conductive part undergoing inspection and driven by an alternating current source to create a flux of magnetic field into and below the conductive surface. This flux causes local current to flow in a conductive part. This local current flow induces a mutual magnetic flux of its own. A complementary coil, the sense coil, operates to receive current mutually induced by the resultant flux due to current flow through the conductive part. Coupling between the coils occurs through the conductive part itself. Any flaw or defect in the near surface integrity of the conductive Dart will disrupt the flow of induced current. This disruption can be detected as a change in voltage detected by the sense coil.

A standard eddy current inspection instrument typically utilizes probes made by various manufacturers including: Staveley, Uniwest, Foerster and NDT Product Engineering. Such probes generally have coil elements operating as drive and sense coils which are disposed in close proximity of one another. The probes may differ in their winding arrangement and coil connections. The coils may be wound in the same or opposite directions to accomodate additive or subtractive response signal sensitivity. For example, split core differential probes have coils wound in the same direction while recording head probes have coils wound in opposite directions. Subtractive or "differential" probes generally operate using an impedance mode of detection utilizing a bridge circuit. Differential probes are sensitive to in plane flaw detection making them useful for eddy current testing, although bridge circuit detection can be a disadvantage. One advantage of probes operating in reflection mode is that drive and sense signals on respective coils are more easily separable than they are if a bridge circuit mode of detection is used with a differential sense coil configuration. Typical sense coil configurations include absolute and differential configurations. Absolute configuration utilizes a fixed reference for detection making it useful for calibration. Differentially configured probes utilize a bridge circuit for detection referenced only to ground. Response signals are collected from probes by using manual or mechanical scanning modes. Drive coils can typically be configured as individual coils or in a continuous, serpentine line providing uniform, adjacent, parallel segments driven by an external alternating current source. It is also possible to operate as drive and sense with the same coils using a bridge circuit configuration.

Scanning along the surface of the conductive part being inspected is typically accomplished by moving a probe across a conductive surface to cover all regions of interest. Inspection systems often display a single probe's time trace decomposed into complex sinusoidal components: an in phase component (I), and a quadrature component (Q). Component display is accomplished using an oscilloscope or strip chart recorder. A primary problem in utilizing signal thresholding to determine if a flaw is present somewhere along the scan path involves distinguishing the disruptive flaw signal above background noise. The problem is complicated further as eddy current probes are themselves a source of great variability. Imaging using this approach to measurement collection by scanning with a single probe is time consuming and labor intensive. Furthermore, the image so obtained is spatially blurred by the overwhelming relative size difference between the probe and the flaw to be detected. The use of an inherently spatially correlated measurement array provides simultaneous acquisition of discretely collected data for a plurality of measurements in a single scan. Inspection surface scanning requirements using a spatially correlated measurement array become one dimensional rather than two dimensional as with a single probe. An array spatially correlates one dimension in terms of the other; thus, data collection in one dimension is inherently acquired by scanning in the other. The effective removal of an additional scanning dimension is predicated on providing a spatially correlated measurement array of substantially identical probe elements. One dimensional scanning using such an array is much faster.

Probe sensitivity to small flaw detection is limited by the size of the probe sense coil. The need for miniaturization to reduce this size and improve flaw detection sensitivity has been recognized. However, with conventional fabrication technology the miniaturization required cannot be achieved. In addition to providing decreased probe size relative to that of the flaw, the probe array elements must be substantially identical. Such provisions have not been possible with conventional coil fabrication techniques.

Furthermore, conventional scanning cannot be applied to a wide class of geometrically difficult inspection surfaces. Traditional probe arrays lack a flexible feature that would accomodate scanning such geometries. Scanning with conventional probe arrays lack an alignment feature; thus, alignment becomes time intensive, detracting from useful scan time.

OBJECTS OF THE INVENTION

An object of this invention is to provide a multi-layer, integrated, spatially correlated probe array.

Another object of this invention is to provide a probe array comprising precisely fabricated, substantially identical probe elements.

Yet another object of the invention is to provide probe elements small enough to detect flaws heretofore undetectable.

A further object of the invention is to provide a virtual ground, or mutual reference potential, between selectively interconnected probe elements.

Still another object of the invention is to provide a probe array with sufficiently distributed probe elements disposed in a manner to accommodate data collection in a single unidirectional scan of the inspection surface.

Yet another object of the invention is to provide an eddy current probe array with a flexibly conforming feature in order to accommodate difficult inspection surfaces.

A further object of the invention is to minimize registration and alignment problems commonly associated with conventional scanning.

A still further object of the invention is to provide a probe array which can improve inspection speed, accuracy, resolution and reliability.

SUMMARY OF THE INVENTION

The present invention is generally directed to eddy current probe arrays and more particularly directed to an integrated, microelectronic component probe array comprising a plurality of interconnected, miniaturized, sufficiently distributed eddy current probe elements. More specifically, such arrays are fabricated within a flexibly conforming structure using High Density Interconnect (HDI) precision processing. The HDI integrated component fabrication process provides precision, multi-layer, multi-turn probe array elements that are substantially identical and their respective electrical connections. The component probe elements are comprised of component coil elements whose windings can be made small enough, using HDI fabrication, to detect flaws heretofore undetectable by conventional probes. The use of a probe array speeds up data collection as well. The probe array is fabricated into a plurality of small, flexibly interconnected, virtually grounded eddy current coil elements to provide a flexible, two-dimensional probe array which can be affixed to a conforming surface to accommodate inspection of irregular conductive surfaces as a spatially rigid "array probe". The conductive surface is brought within range of the probe sensitive surface of the array for scanning. The elements of the plurality are disposed in an array deposited between flexible, multiple fabrication layers being connected therethrough and affixed to a flexible substrate. The plurality of substantially identical elements are sufficiently distributed to adequately inspect an area of conductor corresponding to the collective width of the active array surface in a single scan. Surface scanning to simultaneously inspect large or geometrically difficult conductive surfaces is made fast and reliable by use of such an array probe. Time required for scanning and reconfiguration is reduced. The size, shape and excitation drive of each of the plurality of probes of the array can be predetermined as a matter of design choice to accommodate changing inspection requirements. Taken together these features provide an eddy current array probe capable of collecting a discrete plurality of spatially correlated probe measurements in a single unidirectional scan of large or irregular conductor surfaces for parallel image processing e.g. by an automated eddy current inspection system. The probe array collects measurements in a manner that can be suitably formatted into discretized signals for image processing to provide flaw detection, characterization and resolution heretofore unattainable using conventional probe scanning schemes.

BRIEF DESCRIPTION OF THE DRAWINGS

While the novel features of the invention are set forth with particularity in the appended claims the invention, both as to organization and content, will be better understood and appreciated, along with other objects and features thereof, from the following detailed description taken in conjunction with the drawings in which:

FIG. 8(d) is a crossectional view of the multi-layer structure of FIGS. 8(b) and 8(c) taken as indicated at 85;

DETAILED DESCRIPTION OF THE INVENTION

Figure 1:
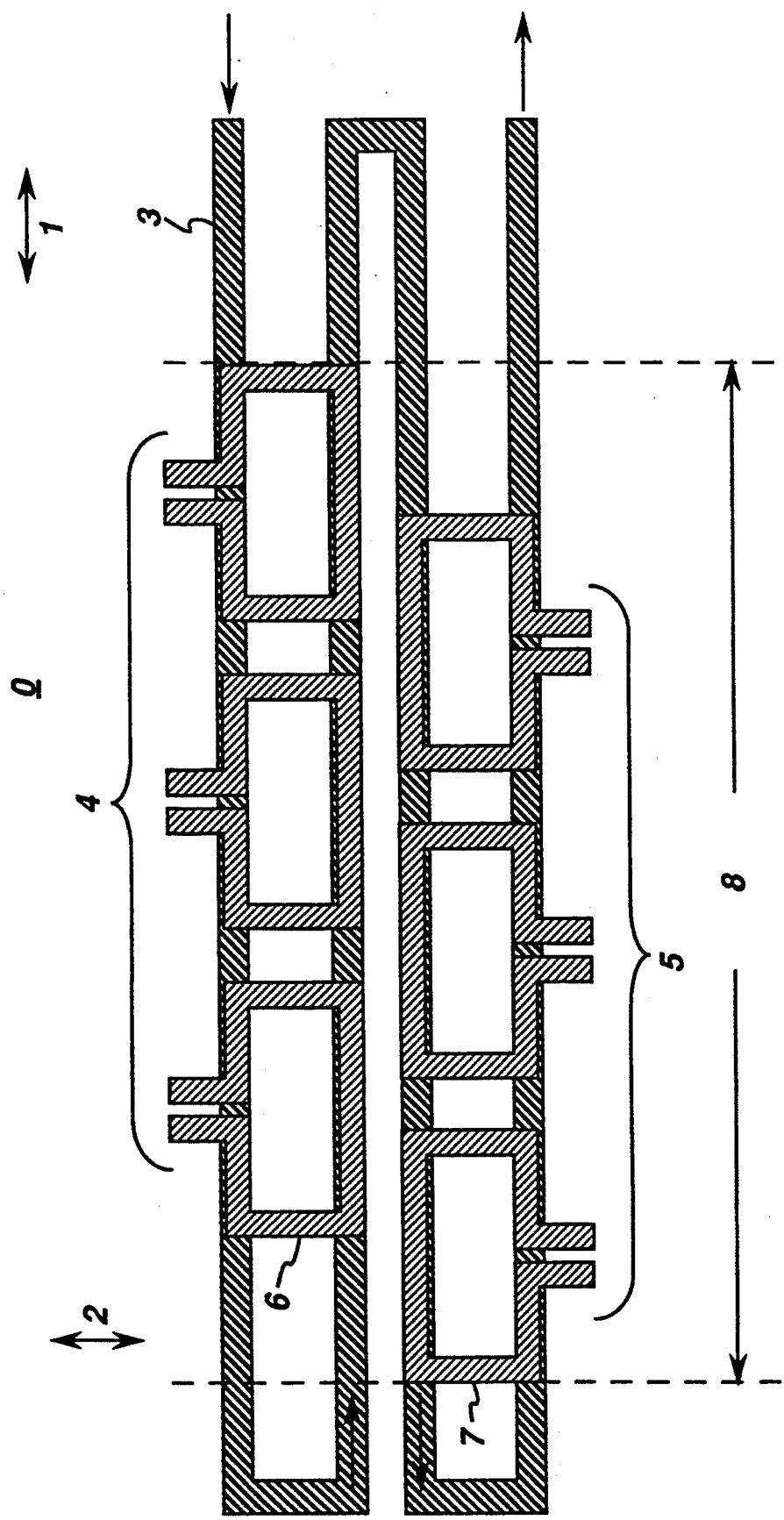
FIG. 1 is a schematic top planar view of an eddy current probe array having one serpentine drive element providing parallel segments in a first layer and six, single-turn, single layer, sense coil elements in at least a second layer made in accordance with present invention.

FIG. 1 shows a top planar view of a simple multilayer eddy current probe array 0 comprising six, single-turn, single layer sense coil elements in absolute configuration, utilized in conjunction with a continuous, serpentine, drive coil element 3 having parallel segments. This is a very simple probe array design presented for the purpose of illustrating that drive and sense elements can be configured in other than conventional "coil" configurations. Obvious coil windings are not necessarily characteristic of eddy current probe array elements. The drive coil element is shown as a lightly shaded line 3 with the instanteous current direction identified by arrows. The six sense coil elements are substantially identical single-turn coils indentified by darker shaded, narrower lines, one of which is identified at 6. The drive coil element 3 is disposed in a first layer and the sense coil elements are disposed in at least a second layer of a multi-layer structure 0. The relative width of said coil elements can be the same or different. In FIG. 1, the identical vertical probe array elements are staggered with respect to one another. Relative staggering of each probe element 6 with respect to a vertically adjacent probe element 7 is accomplished in direction 1 which identifies the preferred scanning direction indicated by arrow 2. Staggered offsetting of probe elements 6, 7 provides complete scanning coverage in direction 2 and avoids null positions which lack sensing capability. The probe array can cover a scan width given by the collective probe active width which is herein indicated at 8. Electrical contact pads for making electrical connections to the array are often segregated into specific locations. Such specific locations are identified on either side of the array as indicated at 4, 5.

Figure 2A:
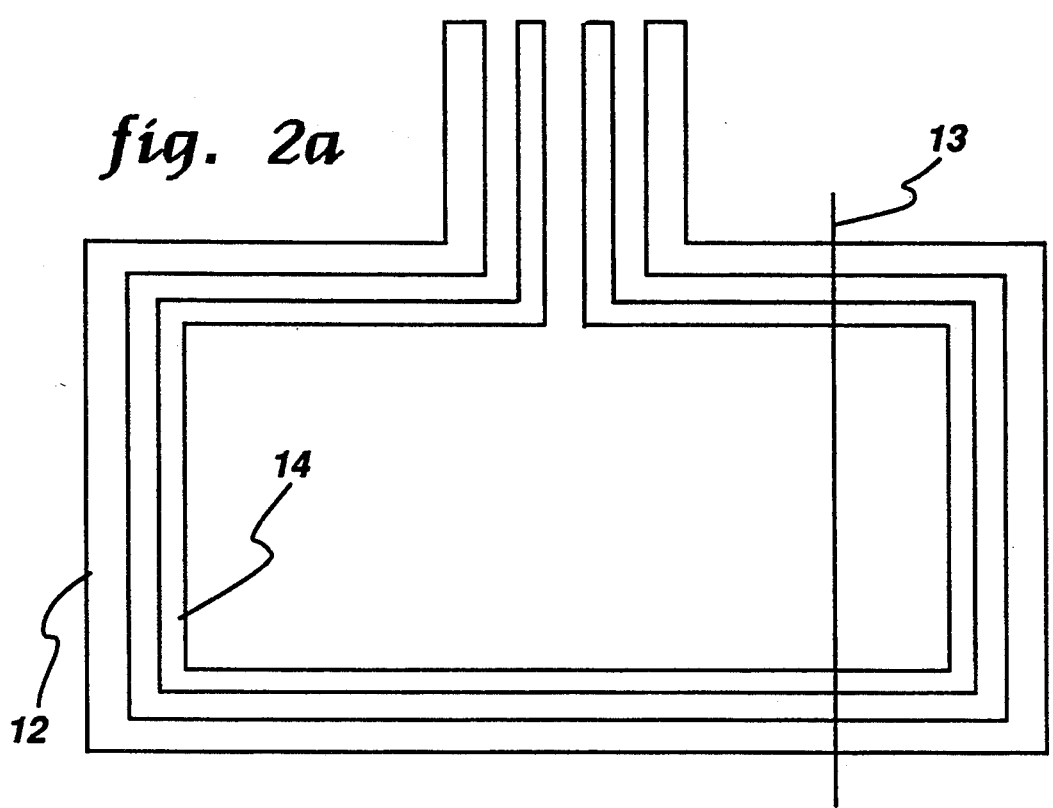
FIG. 2(a) is a schematic top planar view of a single layer, single turn drive element and an associated single layer, single turn sense element fabricated in the same layer in accordance with the present invention.
Figure 2B:
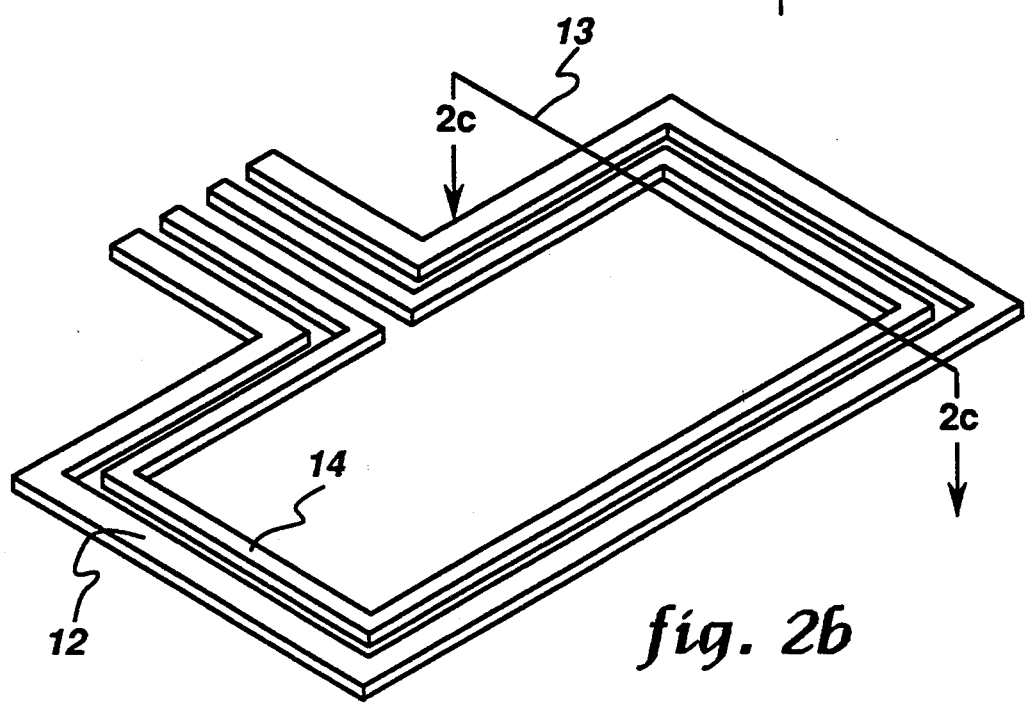
FIG. 2(b) is a perspective view of a single layer, single turn drive element and an associated single layer, single turn sense element fabricated in the same layer in accordance with the present invention.
Figure 2C:
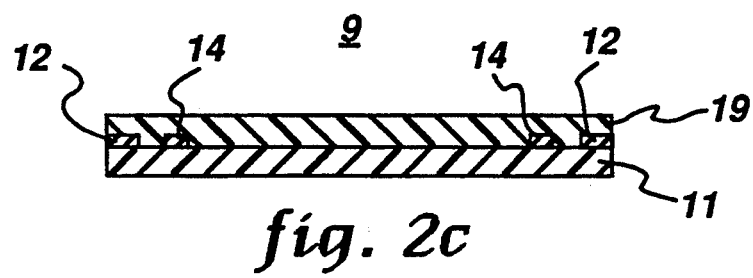
FIG. 2(c) is a crossectional view through the structure of FIGS. 2(a) and 2(b) taken as indicated at 13.
Figure 3A:
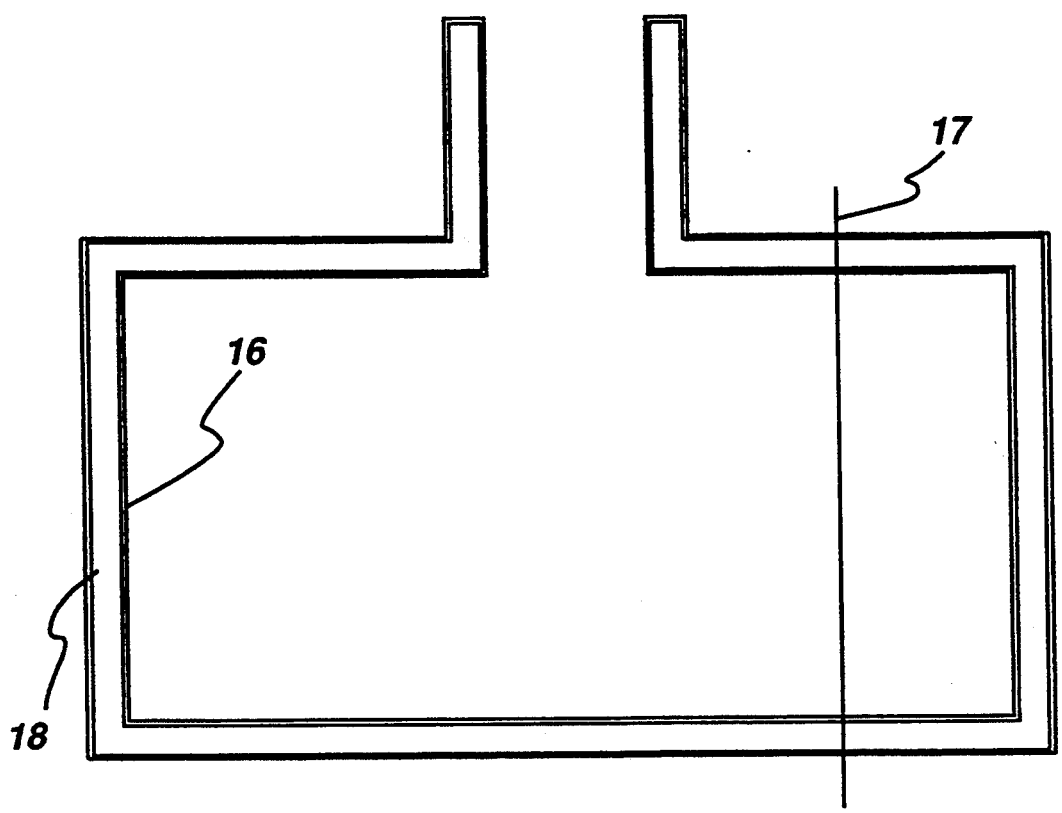
FIG. 3(a) is a schematic top planar view of a single layer, single turn drive element and an associated single layer, single turn sense element fabricated in a different layer in accordance with the present invention.
Figure 3C:
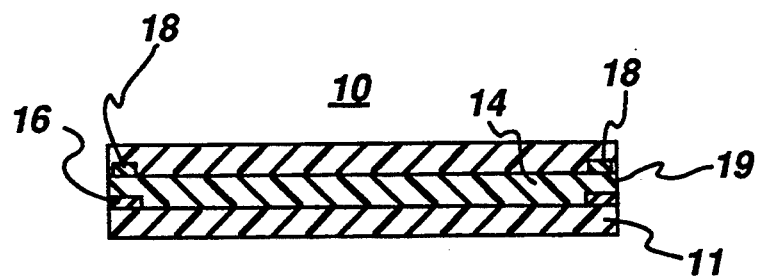
FIG. 3(c) is a crossectional view through the structure of FIGS. 3(a) and 3(b) taken as indicated at 17.
Figure 3B:
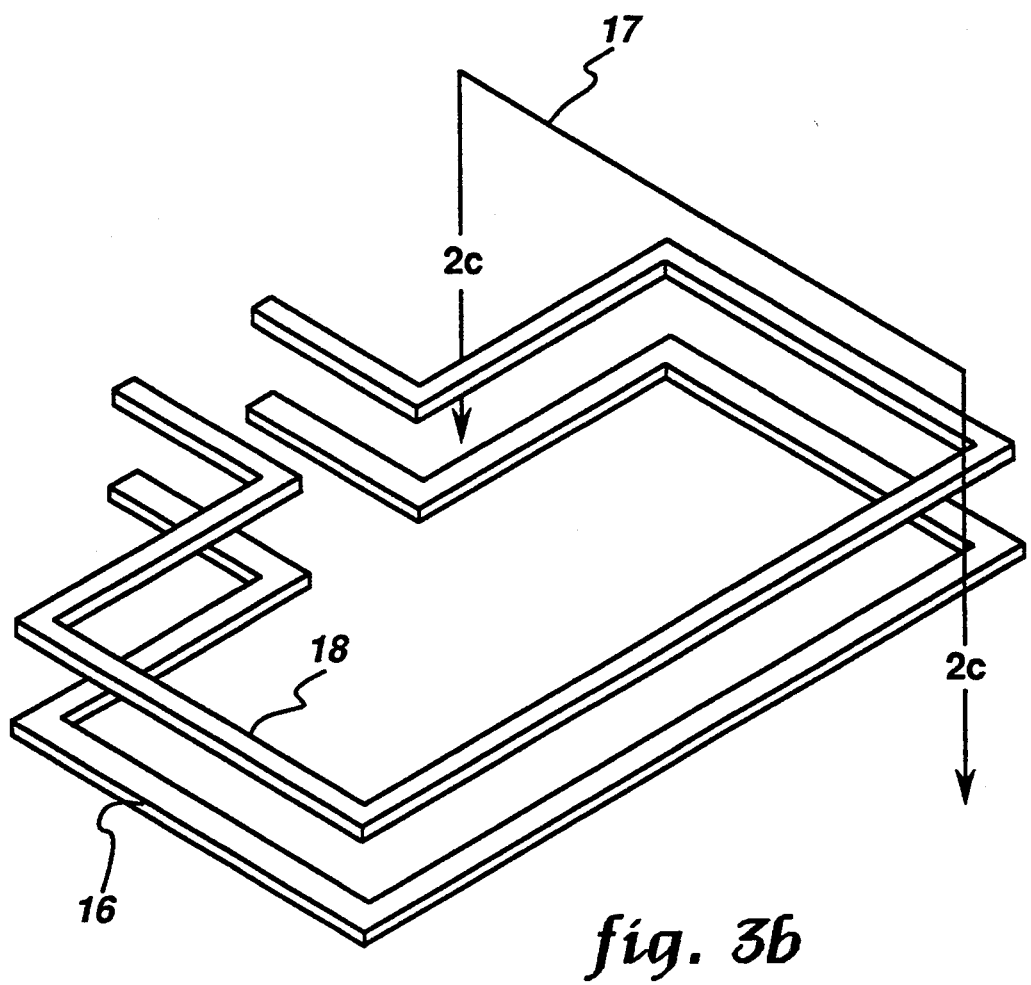
FIG. 3(b) is a perspective view of a single layer, single turn drive element and an associated single layer, single turn sense element fabricated in a different layer in accordance with the present invention.

FIG. 2(a) and 2(b) illustrate a very simple drive and sense element fabricated in the same layer in both top planar and perspective views while FIG. 2(c) illustrates a cross section through the simple drive and sense element which have been fabricated into a single layer structure using High Density Interconnect multilayer fabrication technology. In the top planar view of FIG. 2(a), these elements are distinguished by light and dark shading, although either element can operate as a drive or sense element. In the interest of visual clarity, the elements shown are of differing metallized segment widths. This is simply a convenience for the sake of illustration and does not preclude segment elements of equal widths. These very simple sense and drive elements are presented to help visualize intra-layer and inter-layer disposition of probe elements in order that more complicated configurations can be understood as well. For the sake of illustration in FIGS. 2(a) and 2(b) element 12 is designated as a drive element and element 14 is designated as a sense element. Similarly in FIGS. 3(a) and 3(b) 16 and 18 are designated as drive and sense elements respectively. Effective inductive coupling through the inspection surface requires that sense element segments be positioned in close proximity to drive element segments. The closeness of these elements to one another is seen in FIGS. 2(a) 2(b), 3(a) and 3(b). FIG. 2(c) illustrates a cross sectional view through the single layer structure 9 of FIGS. 2(a) and 2(b) taken as indicated at 13. The single layer structure 9 of FIG. 2(c) is comprised of a flexible substrate 11 such as Kapton ™, a polyimide available from E. I. DuPont de Nemours Company, upon which a metallized pattern comprising sense element 14 and drive element 12 have been disposed either directly or after an initial deposition of an intervening dielectric layer (not shown). This metal pattern disposition is accomplished by first depositing a layer of metallization using sputtering or electroplating techniques to deposit titanium and copper for example, then patterning with a suitable photo resist to radiation expose a pattern of drive and sense elements from the metallized layer. Thereafter, an etching step erodes away all metal but the patterned elements 12, 14. These metallization, patterning and etching steps are accomplished using a photo-lithographic fabrication technique that is capable of achieving precision and uniformity at small dimensions. High Density Interconnect (HDI) technology accomodates such a technique of fabrication. HDI fabrication technology is described in detail in co-pending application Ser. No. 07/504/769 entitled "A Flexible Interconnected System" by Charles W. Eichelberger, et al. The width of sense element segments 14 and drive element segments 12 may be the same or different. After the metallization step, a layer of dielectric 19, like siloxane polyimide, is applied thereupon by spin coating. FIG. 3(c) illustrates a crossectional view taken at 17 through the double layer structure 10 of FIGS. 3(a) and 3(b). A similar fabrication procedure is followed; however the metallization and dielectric application steps are repeated resulting in the multi-layer structure 10 shown. After metal deposition and photo-lithographic patterning of drive element 16 directly (or indirectly) onto flexible substrate 11, a layer of dielectric, like siloxane polyimide, is thereupon applied. Onto this layer of dielectric 19, another layer of metallization is deposited and patterning of sense element 18 is accomplished by photo-lithographic means. Thereafter, another layer of dielectric, like siloxane polyimide, is deposited. Note the width difference and relative offset of sense element 18 compared to drive element 16. FIGS. 2(c) and 3(c) illustrate several interlayer and intralayer configurational options available when flexible multiple layer probe array elements are fabricated using High Density Interconnect fabrication technology. HDI fabrication accomodates a flexible substrate using photo-lithographic means to achieve a level of intricacy and precision heretofore unattainable by conventional means.

Figure 4:
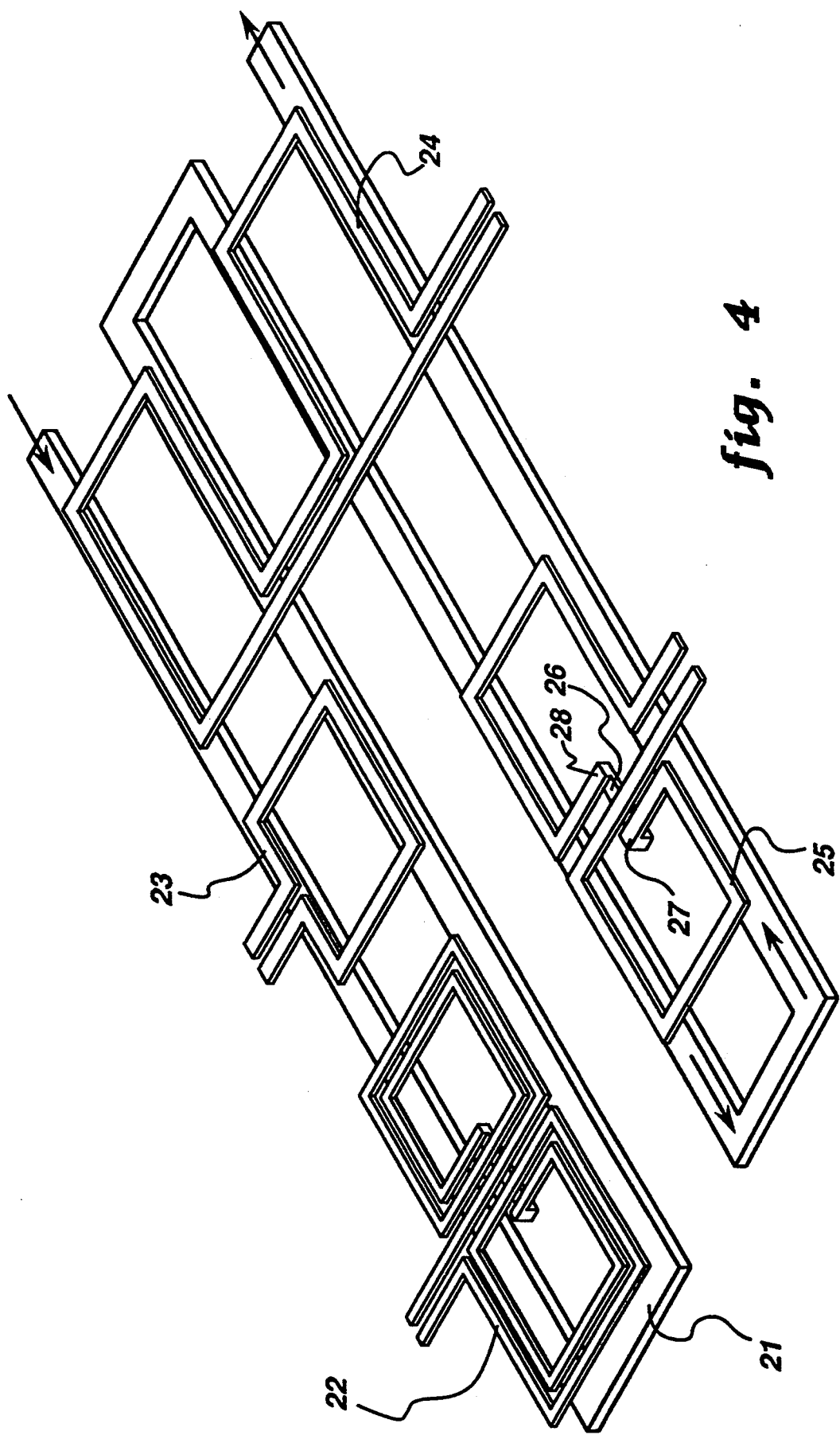
FIG. 4 is a schematic top planar view of an eddy current probe array having a parallel, underlying drive line element with three associated sense elements fabricated in a multilayer structure in accordance with the present invention.

FIG. 4 illustrates some typical elements of a simple eddy current probe array having a single drive element disposed in a back and forth, serpentine arrangement providing long parallel segments disposed in an underlying layer with four associated sense elements disposed in at least another overlying layer. Drive element 21 is lightly shaded in the figure to indicate that it resides in a first layer of a multi-layer structure. Direction of current flow in the drive element is indicated by arrows. The four darker shaded sense elements are herein shown to have narrower metallization widths than those of the underlying drive elements. Various configurations for sense elements in a single layer structure include: a single loop in absolute configuration 23, a double-loop in absolute configuration 24, a single turn, double loop in differential configuration 25 and a double turn, double loop in differential configuration 22. The size of a single loop as well as the number and turns of the loops of a multi-loop sense coil can be varied to design for a particular application. Sense element 23 is a single turn, single layer, sense element in absolute configuration disposed in close proximity to the underlying drive element 21. Sense element 24 is a double turn, single layer sense element also in absolute configuration disposed so that the turn segments of the sense element are proximately positioned near the underlying parallel segments of the drive element 21. A sense element can be characterized by multiple turns connected in various configurations. Sense element 25 illustrates two, single turn, single layer coil elements connected in differential configuration wherein the short segment 26 between the darkened squares 27 and 28 is disposed in a layer other than that layer in which the turns of the coil element reside. When the coil elements are identical, this connection provides a "virtual ground" which operates as a common reference potential given identical induced coil voltages. This eliminates the need for a physical ground connection; thereby inherently improving eddy current probe element design. Interlayer metallization connections at 27 and 28 divert conduction path 26 to another layer to avoid electrically shorting the element. Both turns however, reside in the same layer. A similar coil element comprised of two double turn, single layer coil windings connected in differential mode is illustrated at 22 wherein the double turns of each loop reside in the same layer. These configurations are presented to illustrate the degree of flexibility in probe element design using a layered fabrication technique for producing eddy current probe arrays.

Figure 5:
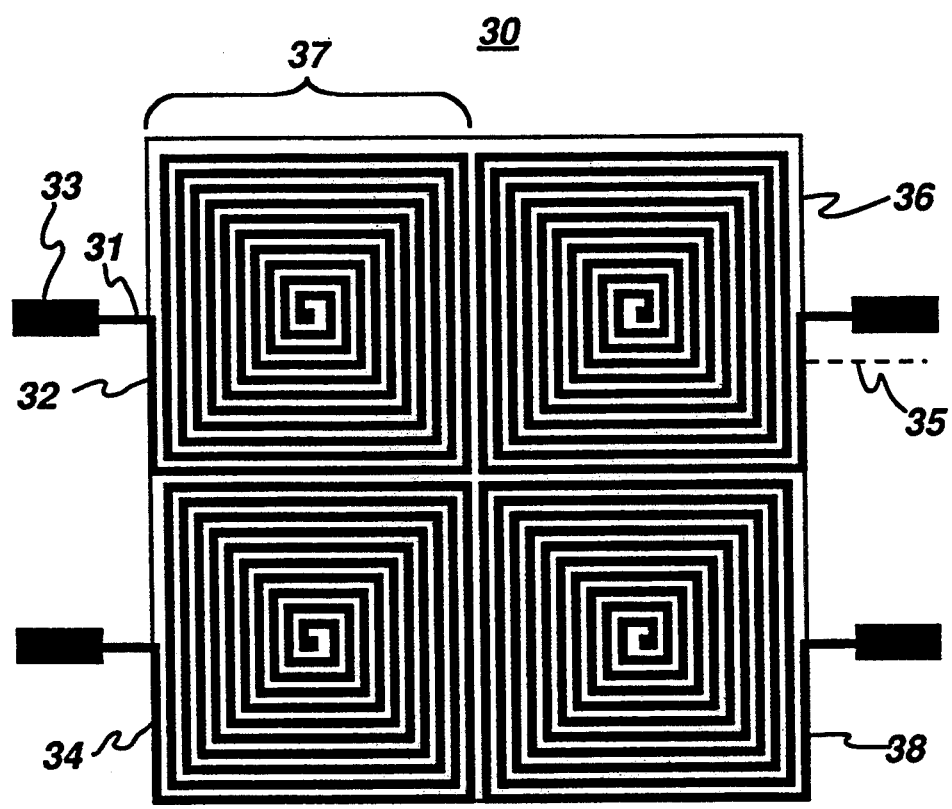
FIG. 5 is a schematic top planar view of four, double layer multi-turn coil elements fabricated in accordance with the present invention.

FIG. 5 is a top planar view of four, double layer, multi-turn, conventional probe array coils, one of which is indicated by numeral 37. The coils are shown in an unstaggered configuration which may not be suitable for use as a probe array but illustrative of the appearance of conventional sense and drive coil elements. Coils 32 and 34 are wound in the same direction while remaining coils 36 and 38 are wound in the opposite direction. A representative connection line 31 electrically connects coil element 32 to respective contact pad 33. Each of the other coil elements 34, 36 and 38 are connected in a similar manner to their respective contact pads. Coils are electrically connected to one another as well as to external current sources and output leads using these contact pads. Probe test element 30 is comprised of two layers, each layer containing four, co-planar coils. The top planar view of FIG. 5 shows only the coils of the top layer 32, 34, 36 and 38. Four similar coils (not shown) are disposed in a layer beneath the one shown in FIG. 5. A representative connection line 35 is identified using a dotted line to illustrate electrical communication to similarly situated underlying coils (not shown) disposed in an underlying layer. Such coils are designated as sense and drive coils by providing appropriate electrical connection thereto. Designated sense and drive coils are proximately disposed with respect to one another in order to provide sufficient inductive coupling through the surface under inspection. Designated sense coils responsively cooperate with designated drive coils when said drive coils are electrically driven by an external alternating current source (not shown). A drive source is connected across a designated drive coil at respective contact pads. Likewise, an output lead is connected across a designated sense coil at its respective contact pads.

Figure 6A:
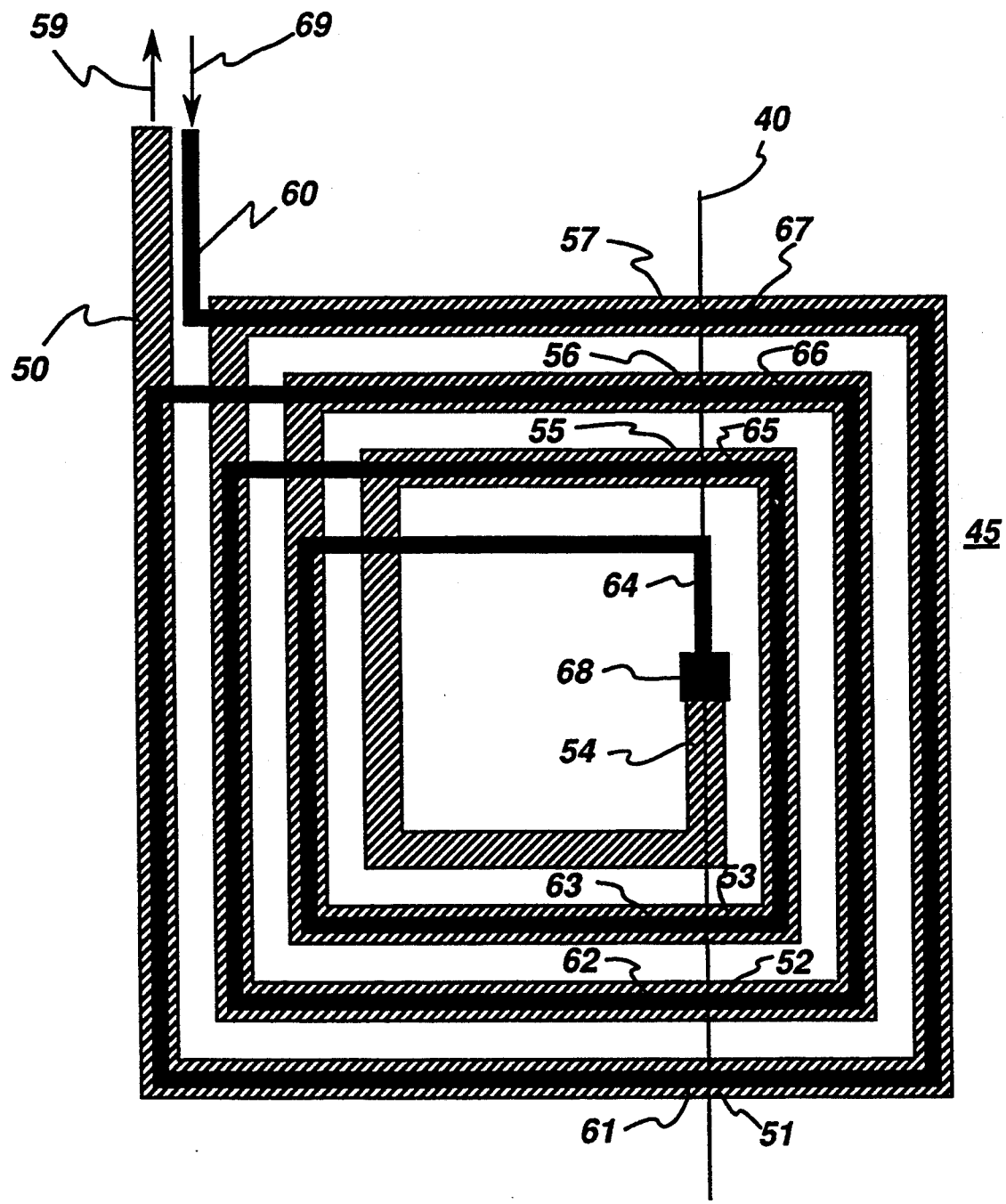
FIG. 6(a) is a schematic top planar view of a double layer, multi-turn coil comprised of two single layer coil elements fabricated in accordance with the present invention.
Figure 6B:
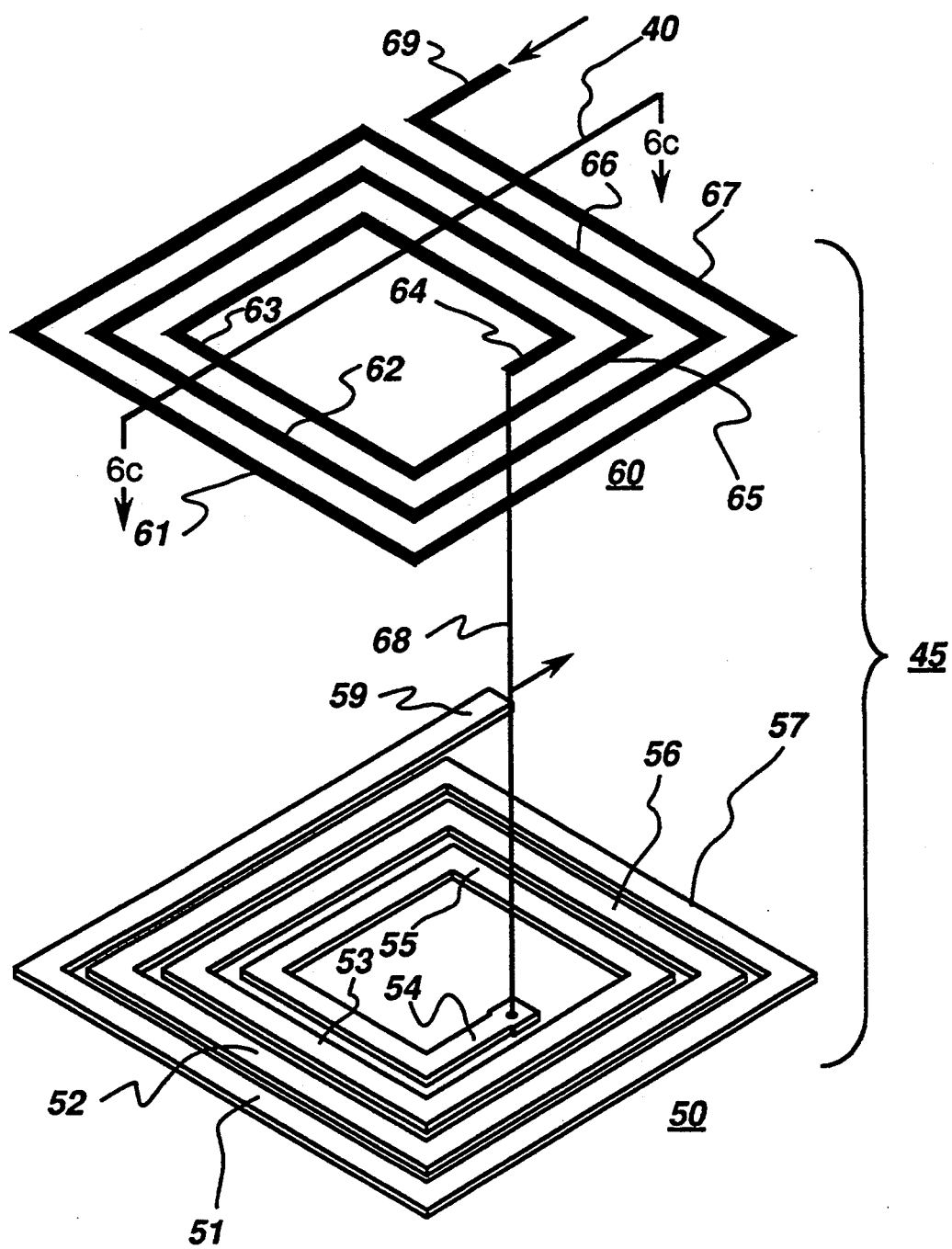
FIG. 6(b) is a perspective view of a double layer, multi-turn coil comprised of two single layer coil elements fabricated in accordance with the present invention.
Figure 6C:
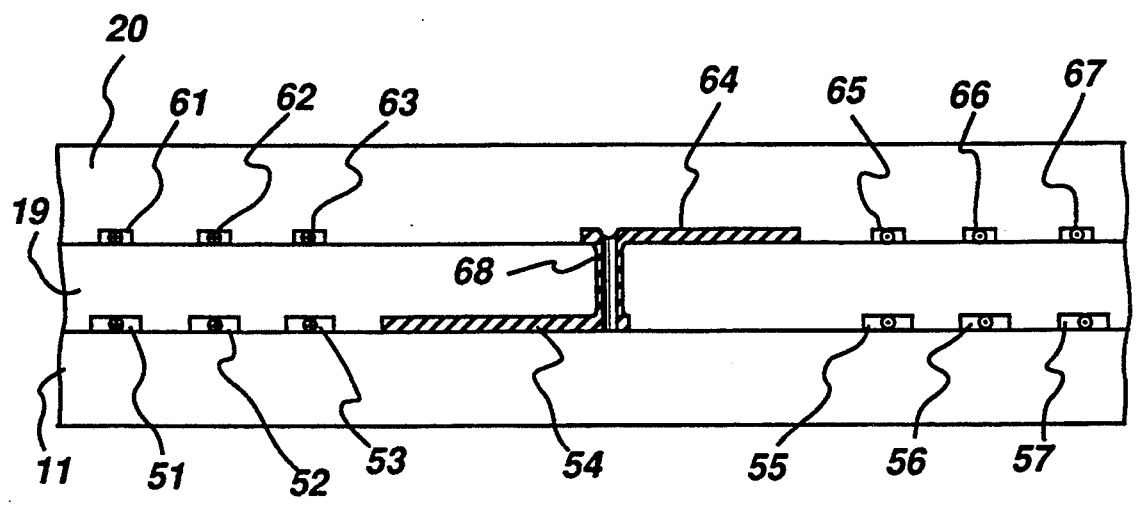
FIG. 6(c) is a crossectional view of the structure of FIGS. 6(a) and 6(b) taken as indicated at 40.

FIG. 6(a) and 6(b) illustrate a top planar and perspective view of a coil element 45 comprised of two. three-turn coil windings 50, 60 disposed in separate but adjacent layers and centrally connected in a serial manner as a probe element. The lighter shaded, wider coil segments of underlying coil winding 50 are disposed as shown in FIG. 6(c) in a first layer 19 beneath a second layer 20 in which coil 60 is disposed. Coil 60 is indicated by darker shaded, narrower coil segments. The darkened square 68 indicates an interlayer electrical connection between respective coil layers 19 and 20. Such a connection is accomodated by laser drilling or chemically forming a precision hole through dielectric layer 19 before a second metallization layer is applied thereon. Arrows 59 and 69 indicate the direction of current flow through coil element 45 at an instant in time. The crossectional view of FIG. 6(c) is taken as indicated at numeral 40 in FIGS. 6(a) and 6(b). The instanteous current flow in each crossectionally viewed coil segment of FIG. 6(c) is identified using engineering conventions, "+", indicating current flow into the plane of the page and, ".", indicating current flow out of the plane of the page. Where possible, numerals identifying coil segments have been preserved in FIGS. 6(a-)-6(c) to facilitate crossectional visualization of the multilayer fabrication of coil element 45 using a High Density Interconnect (HDI) process. The process involves first patterning coil 50 onto a flexible substrate 11 such as Kapton TM, a polyimide available from E. I. DuPont de Nemours Company, which has been bonded to a support carrier (not shown). The support carrier is typically made of Kovar TM steel, to support flexible substrate 11 throughout (HDI) processing in order to avoid shrinking, wrinkling, etc. If desired, substrate 11 could be a ferrite material. Substrate 11 is adhesively laminated to the support carrier by pretreating with a thermoplastic adhesive such as ULTEM TM polyetherimide (not shown) available from the General Electric Company which upon heating will form a reversible bond; thus, permitting easy removal of the flexible substrate 11 from the support carrier after HDI processing but otherwise remaining stable during the fabrication process. Some support means must be provided to support the otherwise flimsy, flexible, ultra-thin eddy current probe array in order to make processing feasible. The flexible Kapton substrate 11 is usually, 12.5–25 microns thick. A metal etched photo-lithographic procedure is used to apply a metallized pattern. Application of a metallization layer proceeds by sputtering a metal such as Titanium and Copper followed by electroplating or simply electroplating. Patterning includes forming the first layer of planar three turn coils corresponding to segments 51, 52, 53, 54, 55, 56, and 57 shown in crossection in FIG. 6(c) with instanteous current flow indicated. Depending upon the application, the metallization can be applied directly to the flexible substrate; or an intervening layer of dielectric (not shown) can be deposited onto which coil 50 is then patterned. Patterning is usually accomplished using a laser exposed photolithographic resist process on the metallization which is followed by etching with an etchant like ferric chloride. After patterning of coil 50, a dielectric layer 19, like siloxane polyimide, is spin coat deposited thereon. Each layer of metallized coils patterned directly onto the Kapton substrate 11 (or indirectly onto an intervening dielectric (not shown)) is covered by spin coating thereon a subsequent layer of dielectric, like siloxane polyimide. Alternatively, additional Kapton can be laminated to the structure using siloxane polyimide/epoxy adhesive (not shown). Thicknesses of the metallization layers are approximately 0.2 mils. Widths of metallized coils range from 1-2 mils. Coil winding separation distances range from 1-4 mils. Dielectric layer spacing between interlayer coil windings range from 0.5 to 1.2 mils. If need be, large portions of the dielectric can be removed by laser ablation. Typical electrical connection "via" holes are laser drilled into the applied dielectric layer to align top surface connection sites with appropriate underlying contact pads. Connecting vias provide interlayer electrical connections fabricated by metallization to be substantially normal to the coplanar layers. Most important to note is the serial electrical connection made by central via 68 between double layer coil windings 50 and 60. Typical vias are about 1 square mil in size and downwardly tapered at a slant of about 60 degrees to accommodate uniform metallization coverage. Often a short plasma etch is used to remove debris and residual film from drilled via holes. Laser drilling ensures reliable, precise control of via profiles which are critical to effective electrical connection and coil design. Chemical means also exist to produce suitable vias. After the drilling step, a second metallization layer is similarly deposited using sputtering or electroplating to a depth of about 2-20 microns onto dielectric layer 19 extending into via hole 68 and providing electrical connection to contact pad 54 disposed thereunder. Intricate metallization patterns, like the rectangular windings 61, 62, 63, 64, 65, 66 and 67 of coil 60 are provided by depositing a continuous layer of metal using sputtering or electroplating; then, patterning coil windings using radiation exposed photoresist and etching with a suitable etchant in a photo-lithographic step of the HDI process. Etched metallization strip widths of approximately 0.0015 inch with 0.0035 inch pitch are achievable. Thereupon another insulating layer of dielectric 20 is applied. Current flows in the same direction in coils 50 and 60. The application of a dielectric layer, followed by drilling, metallization, patterning and etching are steps that can be repeated to provide complex, multi-layer structures. The alignment and fabrication of connection pads like 54 is computer controlled, wherein such control is based on positional information, to promote a design layout responsive to thermal dissipation, impedance control, etc. HDI fabrication accomodates a computerized capability for making adaptive interconnections to provide a probe pattern design which compensates for variability in operating characteristics. These adaptive control features provide highly reliable fabrication of precise, high density interconnect eddy current probe arrays quickly, consistently and in bulk. Design dictates where connections can be made although for convenience electrical contacts are usually edge oriented. Connections and mountings can be customized or standard depending on I/O requirements and requirements of the specific application. Conductive leads (not shown) to or from respective vias are patterned as part of each layer's metallization process. Conductive leads transmit signals from various probe element components within a layer to the edge of the HDI structure in order to connect to external current sources, and output devices. Application of the uppermost dielectric 20 constitutes a passivation layer. Laser ablation is sometimes used to carve away multi-layer deposits if necessary. The structure 58 may then be laminated onto a preformed ferrite substrate (not shown). This ferrite may be flexible. The presence of a ferrite backing plate (not shown) operates to intensify magnetic flux penetration into a conductive inspection surface. Depending upon the conductivity of the ferrite, it may be advantageous to interpose a layer of dielectric between the ferrite and the first layer of metal coil windings. The support carrier (not shown) is removed by suitable heating after HDI processing is completed.

Figure 7:
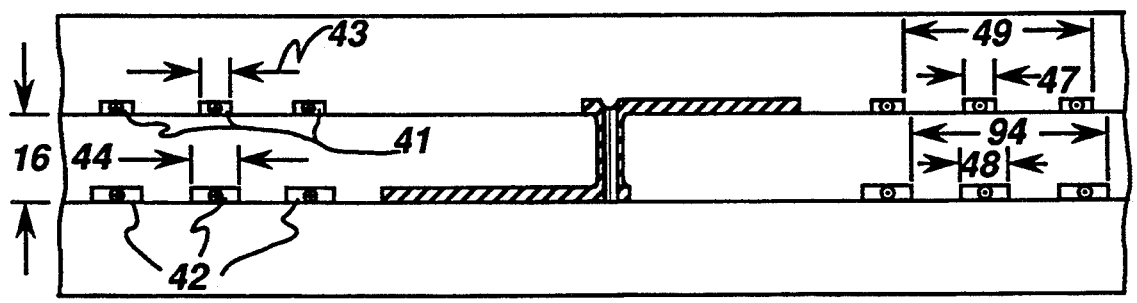
FIG. 7 illustrates offsetting of coil elements and varying widths and spacings of coil elements which are similar to those shown in FIGS. 6(a)-6(c)

FIG. 7 illustrates the option of offsetting coil element windings of one layer 41 with respect to those of another adjacent layer 42. The relative positioning of the metal coil windings with respect to one another governs capacitive coupling between the windings; the strength of which depends on the width 43, 44 of the respective windings and the dielectric separation 46 between them. FIG. 7 also illustrates not only independent choice of winding widths but also inter-winding spacings. Winding width 43, 44 and spacing 47,48 constitute the "pitch" 49, 94 of each coil. The choice of pitch for each coil element is a design choice.

Figure 8A:
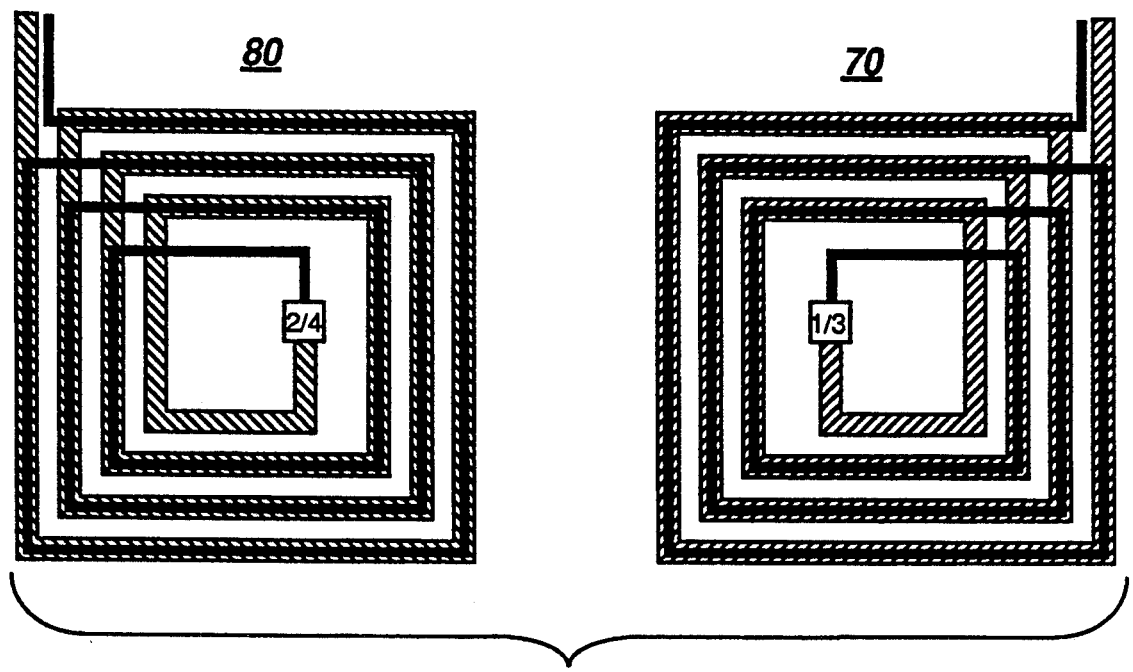
FIG. 8(a) is a schematic top planar view of two, double layer, multi-turn coils each fabricated similarly to the double layer coil of FIGS. 6(a) and 6(b) but having an intervening layer between the coil elements fabricated in accordance with the present invention.
Figure 8B:
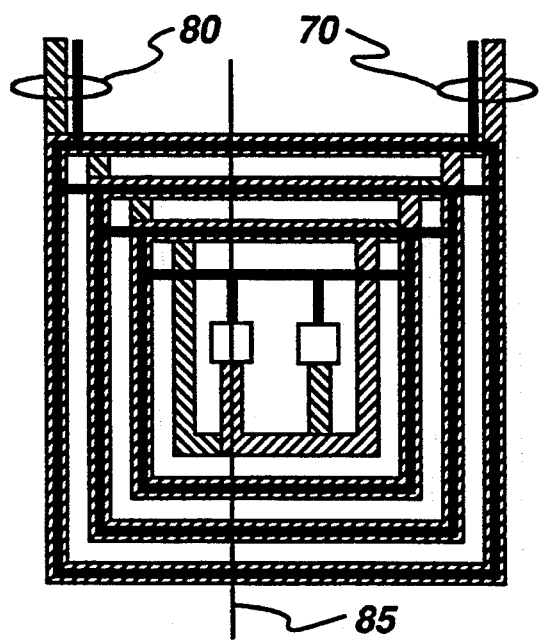
FIG. 8(b) is a schematic top planar view of the two coils of FIG. 7 wherein the lower coil element of the upper coil is disposed in the intervening layer of the lower coil, and the upper coil element of the lower coil is disposed in the intervening layer of the upper coil fabricated in accordance with the present invention.
Figure 8C:
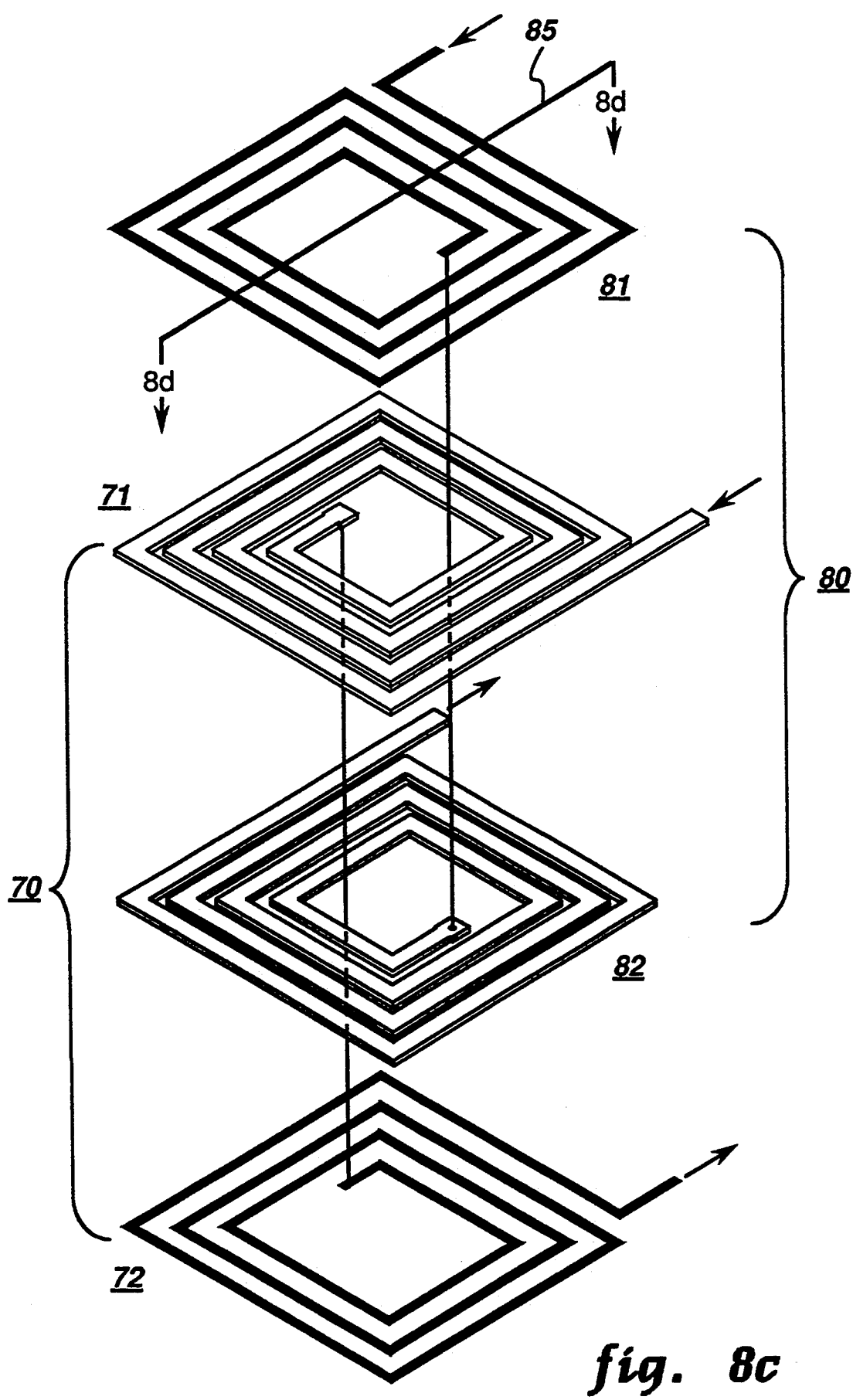
FIG. 8(c) is a perspective view of the two coils of FIG. 7(a) wherein the lower coil element of the upper coil is disposed in the intervening layer of the lower coil, and the upper coil element of the lower coil is disposed in the intervening layer of the upper coil fabricated in accordance with the present invention.

FIG. 8(a) illustrates a top planar view of two, three-turn, double coil elements 70, 80 deposited in separate, though not adjacent, layers. FIG. 8(b) and 8(c) illustrate a top planar and corresponding perspective view of the composite multi-layer structure of coil elements 70 and 80. The crossectional view of FIG. 8(d) is taken at numeral 85 as indicated in FIG. 8(b) and 8(c). Each coil element pair is comprised of two planar coil windings. Coil element 70 is comprised of coil windings 71 and 72 which reside in layers 19 and 74 respectively wherein layer 20 is interposed therebetween. Coil element 80 is comprised of coil windings 81 and 82 residing in layers 75 and 20 respectively wherein layer 74 is interposed therebetween. Each coil element 70, 80 is fabricated to form multi-layer structure 76 in a manner similar to that of FIG. 6(c), but having an intervening layer interposed therebetween; wherein the lower coil winding 82 of the upper coil element 80 is disposed in the intervening layer of the lower coil element 70, and the upper coil winding 71 of the lower coil element 70 is disposed in the intervening layer of the upper coil element 80. The central "via" connection 77 of coil 70 is illustrated in FIGS. 8(b) and 8(c). Current flow is shown by arrows in FIGS. 8(a) 8(b) and 8(c) and indicated using engineering conventions "+" and "." in those coil segments shown in cross section in FIG. 8(d). Again width, separation and relative offset of windings are a matter of design choice tailored to a given application. Either coil could be utilized as a drive or sense coil, depending on which is driven by an external current source (not shown). In fact, both coils could operate as two drive coils, if both are externally driven (not shown); or two sense coils, if both are inductively coupled to an externally driven drive coil. The drive coil may be deposited in the layer furthest from the inspection surface having wider coil width than the underlying sense coil. Delineating drive and sense coils in a particular configuration can establish one surface of the probe array as the probe sensitive surface. Herein, if coil element 80 comprising coil windings 81 and 82 is used for driving while coil element 70 comprising coils windings 71 and 72 is used for sensing surface 83 is established as the probe sensitive surface.

Figure 9:
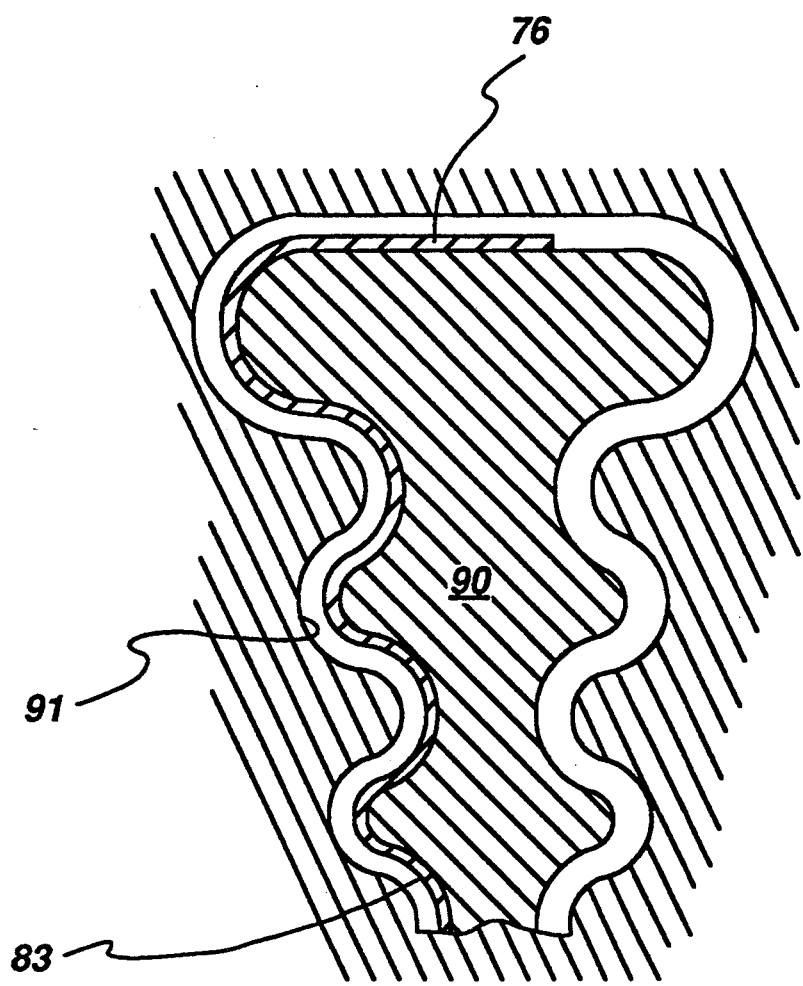
FIG. 9 is a sectional view of a flexible eddy current array probe affixed to a ferrite material made in accordance with the present invention

FIG. 9 illustrates the use of ferrite or some other core material to fashion a scanning form 90 onto which a two dimensional flexible HDI fabricated eddy current probe array 76 can be suitably surface bonded. The probe sensitive surface 83 of the array is exposed in a conforming fashion to the conductive surface 91 under inspection. Conformability is provided by surface conforming form 90, wherein affixed, probe sensitive surface 83 forms an oppositely signed, close fitting complement to the irregular surface under inspection 91. The entire surface or just part of the surface of the surface conforming scanning form 90 may be occupied by the two dimensional, flexible eddy current probe array 76. Affixing the eddy current probe array to scanning form 90 expedites inspection of difficult geometries which cannot be inspected by conventional scanning means. This is particularly useful for accomplishing inspection in an industrial setting. If the inspection surface 91 exhibits translational symmetry along an axis of translation, herein taken to be normal to the plane of FIG. 8, inspection can be accomplished in a single axial translation of form 90 along the inspection surface 91. This presumes the probe sensing elements are sufficiently distributed to provide complete coverage in a single scan.

Other eddy current probe array designs wherein drive and sense coils are not configured in obvious "coil" configurations are within the scope of this invention. Sufficient, uniform drive coverage can be accomplished by configuring the drive coil in long parallel, serpentine drive line segments causing current flow to be alternately oppositely directed in adjacent parallel drive line segments. It is recommended that sense lines be positioned near drive lines to promote coupling; and as already mentioned, staggering of sense coil elements must be sufficient to provide complete scan coverage and eliminate sensitivity nulls. Drive coil design is based on presenting a uniform drive, while sense coil design is typically tailored to the requirements of the inspection application and the specific geometry of the surface under inspection. Sense coils of varying shapes turns and sizes being electrically interconnected in various ways can be disposed in overlapping layers to provide a capability for selectively varying eddy current probe array sensitivity. In this way flux penetration is selectively varied into the inspection surface by selectively driving various coils of the same probe array. This provides an array with an inherent selective sensitivity feature.

When a flexible, HDI fabricated, eddy current probe array is used in conjunction with a multi-channel, multi-frequency eddy current inspection system for industrial non-destructive near surface flaw detection, measurement collection speed and accuracy are improved; thus, increasing inspection productivity. Furthermore, when utilized in conjunction with such a system, flaw detection and characterization are improved through the implementation of parallel signal processing in image processing. These improvements are made possible by simultaneously collecting a plurality of spatially correlated measurements using an eddy current measurement array enabling formatting of the plurality of measurements for parallel image processing.

While a specific embodiment of the invention has been illustrated and described herein, it is realized that numerous modifications and changes will occur to those skilled in the art. It is therefore to be understood that the appended claims are intended to cover all such modifications and changes as fall within the true spirit and scope of the invention.

We claim:

1. A flexible eddy current surface measurement array comprising:

a spatially correlated plurality of electrically interconnected eddy current sensing means wherein said eddy current sensing means comprise drive and sense elements operatively coupled through a conductive surface under inspection such that said drive and sense elements are disposed in at least two layers wherein said elements are electrically interconnected therethrough and within an integral, multi-layer structure such that said multilayer structure is outwardly affixed onto a supporting material having a surface conforming to match the conductive surface under inspection wherein said sense elements are further comprised of a plurality of coil elements such that each of said coil elements are electrically connected to respective output leads; and said multi-layer structure is flexible wherein the plurality of said sensing means are disposed.

2. An array according to claim 1 wherein said drive elements are electrically driven by alternating current driving means.

3. An array according to claim 1 wherein said sense elements are substantially identical.

4. An array according to claim 1 wherein at least one said drive element is disposed in the layer nearest said inspection surface.

5. An array according to claim 1 wherein at least one said sense element is disposed in the layer nearest said inspection surface.

6. An array according to claim 1 wherein at least one said drive element is disposed in the layer furthest from said inspection surface.

7. An array according to claim 1 wherein at least one said sense element is disposed in the layer furthest from said inspection surface.

8. An array according to claim 1 wherein at least one said drive element is disposed in at least one layer interleaved between layers containing at least one said sense element.

9. An array according to claim 1 wherein at least one said sense element is disposed in at least one layer interleaved between layers containing at least one said drive element.

10. An array according to claim 1 wherein at least two of said coil elements are wound in the same direction.

11. An array according to claim 1 wherein at least two of said coil elements are wound in opposite directions.

12. An array according to claim 1 wherein said coil elements are electrically differentially interconnected so as to virtually ground select pairs of identical coil elements by providing a mutual reference potential between said pairs.

13. An array according to claim 1 wherein sense elements are comprised of a plurality of electrically interconnected coil elements disposed in a multi-layer structure.

14. An array according to claim 13 wherein said inter-connected coil elements are skewed relative to one another.

15. An array according to claim 13 wherein said inter-layer coil elements are aligned relative to one another.

16. An array according to claim 1 wherein said array comprises flexible, multiple dielectric layers wherein said elements are affixed to a flexible substrate using a photo-lithographic fabrication process.

17. An array according to claim 16 wherein a first layer of said elements are disposed directly upon said substrate.

18. An array according to claim 16 wherein a first layer of said elements are disposed upon a first dielectric layer disposed directly upon said substrate.

19. An array according to claim 16 wherein said flexible substrate is removably affixed to a support means during processing.

20. An array according to claim 16 wherein said multi-layer structure is affixed to a ferrite backing.

21. An array according to claim 16 wherein said structure is affixed to a flexible ferrite backing.

22. An array according to claim 16 wherein said substrate is a ferrite.

23. An array according to claim 16 wherein said substrate is flexible ferrite.

24. An array according to claim 1 wherein said supporting material is at least in part ferrite.

25. An array according to claim 1 wherein said plurality of sensing means are sufficiently distributed to accommodate complete scanning coverage of the underlying inspection surface.

26. An array according to claim 1 wherein scanning is accomplished in one direction along the inspection surface.

27. An array according to claim 26 wherein scanning coverage is accomplished by incremental scan in a predetermined direction.

28. An array according to claim 25 wherein the distribution is accomplished by relative staggering of said sensing means with respect to one another normal to the scan direction to provide complete scanning coverage of the inspection surface.

29. An array according to claim 25 wherein said plurality of substantially identical sensing means are sufficiently distributed to accomodate complete inspection in one unidirectional scan.

* * * * *